(12) United States Patent
Polston

(10) Patent No.: US 9,636,287 B2
(45) Date of Patent: May 2, 2017

(54) PRIMECOAT COMPOSITIONS FOR PROTEINACEOUS SUBSTRATES AND METHODS OF PRIMING PROTEINACEOUS SUBSTRATES THEREWITH

(71) Applicant: Norman Polston, McKinleyville, CA (US)

(72) Inventor: Norman Polston, McKinleyville, CA (US)

(73) Assignee: Mad River Science, McKinleyville, CA (US)

(*) Notice: Subject to any disclaimer, the term of this patent is extended or adjusted under 35 U.S.C. 154(b) by 0 days.

(21) Appl. No.: 15/040,613

(22) Filed: Feb. 10, 2016

(65) Prior Publication Data

US 2016/0158133 A1 Jun. 9, 2016

Related U.S. Application Data

(62) Division of application No. 13/439,554, filed on Apr. 4, 2012, now Pat. No. 9,271,914.

(51) Int. Cl.
| | |
|---|---|
| *A61K 8/49* | (2006.01) |
| *A61Q 3/02* | (2006.01) |
| *C07D 203/08* | (2006.01) |
| *A61K 8/33* | (2006.01) |
| *A61K 8/34* | (2006.01) |

(52) U.S. Cl.
CPC ............ *A61K 8/4906* (2013.01); *A61K 8/33* (2013.01); *A61K 8/345* (2013.01); *A61Q 3/02* (2013.01); *C07D 203/08* (2013.01)

(58) Field of Classification Search
CPC . A61K 8/33; A61K 8/34; A61K 8/345; A61K 8/49; A61Q 3/00; A61Q 3/02; B05D 1/38; B05D 3/00; C07D 203/08; C08J 7/04; C08J 7/12; C08K 5/3412; C09D 7/04; C09D 179/04; C09D 203/08
See application file for complete search history.

(56) References Cited

U.S. PATENT DOCUMENTS

| | | | |
|---|---|---|---|
| 2,950,197 A | 8/1960 | Allen | |
| 3,264,368 A | 8/1966 | Lane | |
| 3,985,920 A | 10/1976 | Travis | |
| 3,988,516 A | 10/1976 | Miksovsky et al. | |
| 4,032,565 A | 6/1977 | Kilpatrick et al. | |
| 4,547,363 A | 10/1985 | Joos | |
| 4,766,005 A | 8/1988 | Montgomery et al. | |
| 4,863,993 A | 9/1989 | Montgomery | |
| 5,574,083 A | 11/1996 | Brown et al. | |
| 6,015,549 A | 1/2000 | Cowperthwaite et al. | |
| 6,406,775 B1 * | 6/2002 | Houde | B41M 5/52 347/165 |
| 6,482,871 B1 | 11/2002 | Aasen et al. | |
| 9,271,914 B2 | 3/2016 | Polston | |
| 2005/0244363 A1 | 11/2005 | Hossainy et al. | |
| 2009/0035557 A1 | 2/2009 | Hartmann et al. | |
| 2010/0239503 A1 | 9/2010 | Yarbrough et al. | |
| 2011/0039107 A1 * | 2/2011 | Buchholz | C08J 5/12 428/412 |
| 2011/0251332 A1 * | 10/2011 | Allen | C08G 18/6254 524/500 |

FOREIGN PATENT DOCUMENTS

| | | |
|---|---|---|
| CN | 102234496 A | 11/2011 |
| DE | 2118862 A1 | 11/1971 |
| EP | 0325038 A2 | 7/1989 |
| EP | 0507469 A1 | 10/1992 |
| EP | 0530729 A1 | 3/1993 |
| GB | 718063 A | 11/1954 |
| GB | 1344725 A | 1/1974 |
| WO | 9956711 A1 | 11/1999 |
| WO | 2007097921 A1 | 8/2007 |

OTHER PUBLICATIONS

Int'l Search Report and Written Opinion issued Oct. 30, 2013 in Int'l Application No. PCT/US2012/035210.
Hu et al, "Synthesis and characterization of polyfunctional aziridine/polyester microcapsules by multiple emulsion-solvent evaporation method," J. Cent. South Univ. Technol. vol. 18, pp. 337-342 (2011).
Roesler et al, "Tris-3-(1-aziridino)propionates and their use in formulated products," Progress in Organic Coatings, vol. 50, pp. 1-27 (2004).
Office Action issued Mar. 12, 2014 in U.S. Appl. No. 13/439,554 by Polston.
Office Action issued Jan. 16, 2015 in U.S. Appl. No. 13/439,554 by Polston.
Office Action issued Feb. 17, 2016 in EP Application No. 13716931.4.
Office Action issued on Mar. 22, 2016 in CN Application No. 2013800189727.

* cited by examiner

*Primary Examiner* — Anthony J Green
(74) *Attorney, Agent, or Firm* — Panitch Schwarze Belisario & Nadel LLP

(57) ABSTRACT

Compositions containing a solution of a polyfunctional aziridine component in a non-reactive solvent, and methods of applying such compositions to proteinaceous substrates, such as fingernails and toenails, to provide primed substrates which may be further coated.

10 Claims, No Drawings

PRIMECOAT COMPOSITIONS FOR PROTEINACEOUS SUBSTRATES AND METHODS OF PRIMING PROTEINACEOUS SUBSTRATES THEREWITH

CROSS-REFERENCE TO RELATED APPLICATION

This application claims the benefit of the filing date of, and is a divisional application of, U.S. application Ser. No. 13/439,554, filed on Apr. 4, 2012 (now U.S. Pat. No. 9,271,914, issued Mar. 1, 2016).

BACKGROUND OF THE INVENTION

The reparation, adornment, and prosthetic extension of proteinaceous structures, namely, human fingernails and toenails and livestock hoofs, has been a common practice for centuries. Fingernails are currently known to be coated with multicolored nitrocellulose lacquers, repaired with cyanoacrylate adhesives, and extended with the use of acrylic monomer and polymer slurries or doughs that cure by peroxide/amine free radical mechanisms. The nitrocellulose-based lacquers currently in wide use possess the resiliency and toughness to perform this function well. However, such lacquers require very strong and pungent solvents to solvate the nitrocellulose. Thus, there have been several attempts to provide water-based polishes as substitutes for nitrocellulose-based lacquers. Both nitrocellulose-based lacquers and water-based formulations suffer to varying degrees from premature failure as decorative nail coatings. Such failure can take the form of wear at the tip of the nail, chipping from the ends and sides of the nail, to scratching anywhere on the nail. All three modes of failure are the result of catastrophic failure of adhesion between the nail polish and the nail plate (i.e., the proteinaceous substrate).

While cyanoacrylate adhesives for fingernail repair are relatively adherent to a fingernail plate, the acrylic materials employed for the purpose of creating an artificial fingernail prosthesis are not. Only after treatment of the fingernail surface with an unsaturated carboxylic acid, such as methacrylic acid (current commercial embodiments containing in excess of 70 percent methacrylic acid), will such acrylic monomer and polymer slurries or doughs adhere to the nail plate. Such harsh treatment on a relatively fragile surface poses a serious toxicological hazard due to the corrosive nature of the unsaturated carboxylic acids. Other unsaturated carboxylic acids presently being used in such applications include either alone or in part, acrylic acid and beta-carboxyethyl acrylate. Lower concentrations of these unsaturated acids pose a decreased danger to the intact fingernail surface; however, at such lower concentration the adhesion of the acrylic monomer and polymer slurry is minimized or lost completely. An analogous situation exists when attempting to repair a split or fractured hoof in that without the application of the corrosive and possibly toxic levels of unsaturated acids, very poor adhesion results.

Currently, the most widely used method for improving adhesion of nail polishes and prosthetic materials to proteinaceous substrates, such as fingernails and hooves, has been the physical abrasion and roughening of the proteinaceous substrate surface with a file, sand-paper-like, or other abrasive material, and/or the application of unsaturated carboxylic acid solutions (known in the artificial fingernail art as primers), followed lastly by the application of the polish or prosthetic material.

The disadvantages of such prior art adhesion-improvement methods include: (1) too much physical abrasion or roughening of the proteinaceous substrate, particularly a living fingernail, can be harmful to the substrate and surrounding cuticles; (2) in the area of hoof binding, cracks and fissures in the hooves are not readily abraded or roughened due to the inaccessibility of the surface to such abrasive materials and methods; (3) the unsaturated carboxylic acids that are often used (acrylic acid and methacrylic acid), either alone at full concentration of in combination with other diluents, are highly corrosive and can severely damage the protein of a fingernail or hoof or the underlying or surrounding living tissue; and (4) even with such harsh surface preparation as described above, the adhesive bonds obtained with such methods are poor and all too often inadequate to retain the polish or prosthesis for sufficient periods of time or under stress, thus causing the polish to chip and the prosthesis to break off in whole or in part.

Various prior art adhesive compositions and fingernail treatments have been suggested for improving the bond between coatings and the nail plate. For example, fingernail strengtheners deposited from solution are known, but do not improve bond strength. Materials and methods for obtaining high bond strengths to dentin, which is a partially proteinaceous substrate, have been described, but are the addition reaction products of, for example, pyromellitic acid dianhydride and 2-hydroxyethyl methacrylate (PMDM), the addition reaction product of 3,3',4,4'-benzophenonetetracarboxylic dianhydride and 2-hydroxyethyl methacrylate (BTDA-HEMA) and 4-methacryloxyethyltrimellitic anhydride (4-META). Such materials contain harsh unsaturated compounds and also exhibit inferior bond strength improvement compared to the present invention.

In general, prior art materials and methods suffer from a poor combination of toxicity, odor and/or poor adhesion-promoting performance.

BRIEF SUMMARY OF THE INVENTION

The present invention relates materials and methods which provide increased adhesive bond strength between: adhesives, coatings or composites, on the one hand; and proteinaceous substrates such as fingernails, toenails and livestock hooves, on the other hand. The present invention includes materials and methods for providing primed proteinaceous substrates upon which topcoats, composites, adhesives and/or prosthetic extensions can be applied with improved adhesion. Moreover, the materials and methods of the present invention provide nontoxic, odorless, and improved bond strength between adhesives, coatings or composites, and proteinaceous biological substrates and are a significant improvement over the prior art.

Various embodiments of the present invention are directed to compositions which comprise a solution of a polyfunctional aziridine component in a non-reactive solvent capable of solubilizing the polyfunctional aziridine component. Non-reactive solvents suitable for use in the various embodiments of the present invention are non-reactive with the polyfunctional aziridine component. As used herein, "non-reactive solvent," in its broadest sense, refers to any solvent in which a polyfunctional aziridine component is soluble and which does not react with the polyfunctional aziridine component. Preferably, non-reactive solvents for use in the various embodiments of the present invention are polar, aprotic solvents.

Various preferred embodiments of the present invention are directed to compositions which comprise a solution of a polyfunctional aziridine component in propylene glycol mono-methyl ether, wherein the polyfunctional aziridine component comprises pentaerythritol tris(3-aziridinopropionate), and wherein the polyfunctional aziridine component is present in an amount of 2.5 to 7.5% by weight, based on the solution.

Various other embodiments of the present invention are directed to methods which include: (a) providing a solution of a polyfunctional aziridine component in a non-reactive solvent; and (b) applying the solution to a proteinaceous substrate. Further embodiments of the present invention are directed to methods which include: (a) providing a solution of a polyfunctional aziridine component in a non-reactive solvent; (b) applying the solution to a proteinaceous substrate; (c) removing the non-reactive solvent from the solution applied to the proteinaceous substrate to provide a primed substrate; and (d) applying a topcoat composition to the primed substrate.

In various preferred embodiments of methods according to the present invention, the non-reactive solvent comprises propylene glycol mono-methyl ether, the polyfunctional aziridine component comprises pentaerythritol tris(3-aziridinopropionate), the polyfunctional aziridine component is present in an amount of 2.5 to 7.5% by weight, based on the solution, and the topcoat composition comprises a water-based nail polish.

Briefly, methods in accordance with the present invention can preferably be carried out by applying, e.g., via brushing, a solution of a polyfunctional aziridine component in a non-reactive solvent to a proteinaceous substrate such as, for example, a fingernail, allowing the non-reactive solvent to evaporate and subsequently applying a topcoat to the primed substrate. Thus, after priming the surface of a proteinaceous substrate with a composition according to any of the various embodiments of the present invention, the primed surface may then be contacted with an adhesive, coating or composite providing greater adherence of such materials to the primed substrate, than to an unprimed substrate.

DETAILED DESCRIPTION OF THE INVENTION

As used herein, the singular terms "a" and "the" are synonymous and used interchangeably with "one or more" and "at least one," unless the language and/or context clearly indicates otherwise. Accordingly, for example, reference to "a solvent" or "the solvent" herein or in the appended claims can refer to a single solvent or more than one solvent. Additionally, all numerical values, unless otherwise specifically noted, are understood to be modified by the word "about."

Polyfunctional aziridine components suitable for use in the various embodiments of the present invention include compounds having two or more aziridine functionalities, mixtures containing at least one such compound, and mixtures of two or more such compounds. As used herein, an "aziridine functionality" refers to an aziridine moiety (also referred to in the literature as azacyclopropane, or ethyleneimine) bound to the remaining portion of the compound at the ring nitrogen. The structure of an aziridine functionality is shown below:

wherein either or both ring carbons may be substituted or may both bear two hydrogen atoms. As used herein, unless a specific compound is recited, reference to "aziridine functionality" or "aziridine functionalities" can mean either an unsubstituted azacyclopropane group or an azacyclopropane wherein either or both ring carbons are substituted. In various preferred embodiments according to the present invention, aziridine functionalities present in a polyfunctional aziridine component are unsubstituted.

Compounds having two or more aziridine functionalities which are suitable for use in the various embodiments of the present invention can thus be represented by the following structural formula:

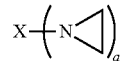

wherein X represents an organic residue, the azacyclopropane carbons may be substituted or unsubstituted, and a represents a number greater than or equal to 2. The organic residue may be linear or branched aliphatic, cycloaliphatic, aromatic, polycyclic, may be substituted or unsubstituted, may contain one or more heteroatoms, and may bear one or more additional organic functional groups which have low nucleophilicity and bear no labile hydrogens (i.e., are non-reactive with aziridine). Thus, compounds having two or more aziridine functionalities which are suitable for use in the various embodiments of the present invention include organic compounds having two or more aziridine functionalities bound thereto.

Preferably, polyfunctional aziridine components suitable for use in the various embodiments of the present invention have three or more aziridine functionalities. Mixtures of compounds, the mixture having an average aziridine functionality of greater than 2.0, can be used and can be prepared, for example, by reaction of branched polyfunctional acrylates and aziridine or by reaction of branched polyfunctional alcohols and aziridinylcarboxylate compounds, such as described in R. Roesler, et al., "Review: Tris-3-(1-aziridino)propionates and their use in formulated products," PROGRESS IN ORGANIC COATINGS, 50 (2004), pp. 1-27, the entire contents of which are incorporated herein by reference. Such mixtures of compounds with two or more aziridine functionalities can be obtained commercially as well, such as PZ-33™ polyfunctional aziridine, available from PolyAziridine, LLC, Medford, N.J.

In general, any organic molecule (e.g., aromatic, aliphatic, heterocyclic, etc.) containing two or more appropriate functional groups can be converted into an aziridine-functionalized organic compound which is suitable for use in the various embodiments of the present invention as a polyfunctional aziridine component. Aliphatic organic compounds are preferable and, even more preferably, branched aliphatic organic compounds can be used as starting compounds for aziridine-functionalization. Lower molecular weight, branched, aliphatic organic compounds, with improved solubility in water-miscible solvents and lower viscosity, can be used as starting compounds for aziridine-functionalization in various particularly preferred embodiments. For example, N-substituted aziridines can be prepared, using an organic compound containing two or more appropriate functional groups as a starting compound, by the addition of alkyl nitrenes to double-bonds present in such an organic starting compound. Suitable polyfunctional aziridine component can also be prepared by the Michael addition of aziridine or methyl aziridine to an ethylenically unsaturated moiety of an organic starting compound. Another suitable general method of preparation for polyfunctional aziridine components according to the various embodiments of the present invention, which is preferred because of the commercial availability of starting materials, is the transesterification of polyhydric branched aliphatic organic molecules with aziridine-modified esters. One specific example of such a transesterification method is the preparation of pentaerythritol tris(3-aziridinopropionate):

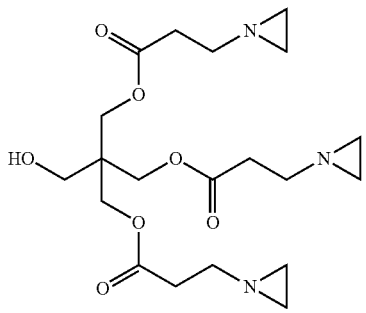 [SMILES: O=C(CCN1CC1)OCC(CO)(COC(=O)CCN1CC1)COC(=O)CCN1CC1]

a multifunctional aziridine compound, synthesized by the transesterification of pentaerythritol with methyl 3-aziridinylpropionate. Preferred polyfunctional aziridine components for use in the various embodiments of the present invention contain pentaerythritol tris(3-aziridinopropionate), trimethylolpropane tris(3-2-methylaziridino)propionate, and/or trimethylolpropane tris(3-aziridinopropionate). Particularly preferred polyfunctional aziridine components for use in the various embodiments of the present invention contain pentaerythritol tris(3-aziridinopropionate).

In the various embodiments according to the present invention, a compound having three or more aziridine functionalities is preferably employed. In various even more preferred embodiments of the present invention, a mixture of two or more compounds having aziridine functionalities, the mixture having an average aziridine functionality of greater than 2.0, is employed. In progressively more preferred embodiments of the present invention, a mixture of two or more compounds, the mixture having an average aziridine functionality of greater than 3.0, more preferably greater than 3.1, even more preferably greater than 3.2, and still more preferably at least 3.3, is employed. For example, pentaerythritol tris(3-aziridinopropionate) synthesized by the transesterification of pentaerythritol with methyl 3-aziridinylpropionate will generally result in a mixture of mono-, di-, tri- and tetra-(3-aziridinopropionate) functionalized compounds, as well as some potential residual pentaerythritol. Preferably, the ratio of these species within the reaction product provides an average aziridine functionality of greater than 3.1, more preferably greater than 3.2, and even more preferably at least 3.3.

In general, the molecular weight of the polyfunctional aziridine components suitable for use in the present invention is not critical, except that the molecular weight should not be so high that the component cannot be rendered into solution using standard mixing equipment (i.e., the molecular weight should not be so high that the component is too viscous or insoluble in the preferred solvents). For example, when employing a polyfunctional aziridine component prepared via transesterification of polyhydric branched aliphatic organic molecules with aziridine-modified esters wherein a mixture of compounds results, the mixture should generally have a viscosity below 5000 centipoise at 25° C., and preferably less than 4000 centipoise at 25° C.

Monomeric ethylenimine ($C_2H_5N$), (i.e., azacyclopropane unbound to any larger molecule) is undesirable from a toxicity perspective. Accordingly, it is generally preferable to use polyfunctional aziridine components which have a low content of monomeric ethylenimine, and even more preferably, polyfunctional aziridine components which have no detectable content of monomeric ethylenimine.

Solvents suitable for use in solutions in accordance with various embodiments of the present invention include any non-reactive solvents capable of solubilizing the polyfunctional aziridine component. As used herein, the term "non-reactive" refers to a lack of reactivity between the solvent and the polyfunctional aziridine component. Protic solvents activate the aziridinyl group to nucleophilic ring-opening and are thus to be avoided. In this regard, as used herein, "non-reactive" refers to and includes aprotic solvents which possess weakly nucleophilic oxygen atom(s) in the form of ether and/or sterically hindered hydroxyl functionalities which do not react with the aziridinyl groups of the polyfunctional aziridine to any appreciable extent. Alkylation of propylene glycol ethers usually favors alkylation of the primary alcoholic moiety in a step-wise process to full alkylation of both primary and secondary alcoholic functions. This minimizes the primary alcoholic functionality as a source of unproductive side reactions with the aziridinyl groups of the polyfunctional aziridine so that mono-substituted propylene glycols can be used for purposes of this invention. Thus, non-reactive aprotic solvents which are suitable for use in the various embodiments of the present invention include aliphatic alkyl mono- or di-substituted glycol ethers wherein at least the primary alcoholic functionality/ies is/are alkylated, e.g., di-substituted mono- and diethylene glycols, and mono- and di-substituted mono- and dipropylene glycols.

Solvents which are capable of solubilizing the polyfunctional aziridine component will possess solubility parameters that closely match that of the polyfunctional aziridine. This measure of cohesive energy density focuses on the principle that substances which exhibit similar solubility parameters—the sum of their non-polar interactions, polar interactions and hydrogen bonding characteristic—are more mutually soluble. Solubility parameters may be calculated from chemical structure wherein the individual molar attraction constants of each functional group are additive over the structural formula For the purposes of the present invention it has been found that the preferable balance of functionality as determined from solubility parameter calculations is manifest in the monoalkylated mono- and di-ethylene and propylene glycols. Higher molecular weight alkylene glycols with a lower ratio of hydroxyl/alkylene ether functionality do not yield solutions of the desired clarity and are thus less preferred.

In various preferred embodiments of the present invention, suitable solvents are additionally fast evaporating. Generally, "fast evaporating" in the context of the present invention refers to a solvent which when applied to a proteinaceous substrate as a thin film of 10 microns or less will evaporate within about 30 seconds. In various preferred embodiments of the present invention, suitable solvents are low odor, odorless, or have a pleasant odor. Both fast evaporation rate and low odor emission can be related generally to the boiling point of the solvent. Solvents suitable for use in various preferred embodiments of the present invention have a boiling point of about 150° C. to about 250° C., more preferably 150° C. to 225° C., even more preferably 150° C. to 200° C., and most preferably 150° C. to less than 200° C. As is understood by those skilled in the art, as boiling point decreases, evaporation rate increases and as boiling point decreases, odor emission increases. Accordingly, it is to be understood that the less offensive a particular solvent's odor is, the lower its boiling point may be in use in the embodiments of the present invention as a faster evaporation rate is achieved.

In various preferred embodiments of the present invention, suitable solvents are low toxicity, and even more preferably, non-toxic. U.S. government regulatory agencies have identified the potential of ethylene glycol polyethers to cause reproductive and developmental toxicity and is restricting the use of the dimethyl polyethylene glycol ethers in consumer products beyond those that are already ongoing. Accordingly, in the various embodiments of the present invention, alkyl ethers of ethylene glycol and polyethylene glycol are less preferred as suitable solvents. Propylene glycols, however, do not suffer from such toxicity issues, and are thus, more preferred.

Furthermore, in particularly preferred embodiments of the present invention, suitable solvents are non-reactive, polar and provide excellent solubility for the polyfunctional aziridine component, fast evaporating, low odor and non-toxic.

In various preferred embodiments of the present invention, suitable non-reactive solvents include dialkyl ethers of ethylene and polyethylene glycols, and monoalkyl and dialkyl ethers of propylene glycol and polypropylene glycols, though as discussed above, ethylene and polyethylene glycols are less preferred than propylene and polypropylene glycols. Examples of suitable non-reactive solvents include, but are not limited to, dialkyl ethylene glycol ethers, dialkyl diethylene glycol ethers such as dimethyl diethylene glycol, dialkyl triethylene glycol ethers, propylene glycol methyl ether, dipropylene glycol methyl ether, tripropylene glycol methyl ether, propylene glycol methyl ether acetate, dipropylene glycol methyl ether acetate, propylene glycol n-propyl ether, dipropylene glycol n-propyl ether, propylene glycol n-butyl ether, dipropylene glycol n-butyl ether, tripropylene glycol n-butyl ether, propylene glycol diacetate, dipropylene glycol dimethyl ether, and mixtures thereof. In various preferred embodiments of the present invention, suitable solvents include mono-alkyl ethers of propylene glycol and dipropylene glycol, and even more preferably mono-alkyl ethers of propylene glycol. In certain particularly preferred embodiments of the present invention, the solvent comprises propylene glycol mono methyl ether.

In accordance with various embodiments of the present invention, solutions of any amount of a polyfunctional aziridine component in a suitable solvent, as described above, could be used, though generally at least about 0.5% by weight of a polyfunctional aziridine component is useful to achieve at least some improvement in adhesion and generally more than 10% by weight provides no further improvement. In various preferred embodiments of the present invention, solutions containing 1 to 10% by weight of a polyfunctional aziridine component, based on the weight of the solution, are used. In various more preferred embodiments of the present invention, solutions containing 2.5 to 7.5% by weight of a polyfunctional aziridine component, based on the weight of the solution, are used. In certain even more preferred embodiments of the present invention, the polyfunctional aziridine component is present in the solution in an amount of about 5% by weight.

Solutions for use in accordance with the various embodiments of the present invention can be prepared in any known manner by simply combining a polyfunctional aziridine component in the desired amount with a suitable non-reactive solvent, and allowing the polyfunctional aziridine component to dissolve, preferably with mixing.

In the various embodiments of the present invention, a solution of a polyfunctional aziridine component in a suitable non-reactive solvent in accordance with any of the aforementioned embodiments is applied to a proteinaceous substrate. Substrates upon which a solution can be applied in accordance with the present invention include, but are not limited to, fingernails, toenails and livestock hooves.

As previously mentioned, methods in accordance with various embodiments of the present invention include applying a solution of a polyfunctional aziridine component in a suitable non-reactive solvent to a proteinaceous substrate. Application of a solution can be accomplished in a variety of ways, though preferably by brushing the solution onto the substrate. Additional, suitable mechanisms by which a solution may be applied to a proteinaceous substrate in accordance with various embodiments of the invention include, but are not limited to spraying, dipping, and blotting. In various preferred embodiments of methods in accordance with the present invention, a solution of a polyfunctional aziridine component in a suitable non-reactive solvent is absorbed onto a sponge or other foam applicator and blotted onto a proteinaceous substrate. Application of a solution in accordance with the various embodiments of the present invention is preferably directed primarily to the tip and edges of the proteinaceous substrate, for example, the tip and cuticle areas of a human fingernail. Preferably, the solution is applied as thinly as possible, and ideally at a thickness of 10 microns or less. In the context of the present invention, the application of a thin coating of a solution of a polyfunctional aziridine component in a suitable non-reactive solvent refers to the absence of "pooling" or excess solution which may drip from or accumulate at the tip or edge of a substrate.

After a solution in accordance with any of the various embodiments of the present invention is applied to a proteinaceous substrate, various preferred methods in accordance with the present invention further include removing the aprotic solvent from the applied solution to provide a primed substrate. Removing the aprotic solvent from the applied solution can include evaporation, either under ambient conditions or with heating, for example, via a heat-lamp. The polyfunctional aziridine component bonds to the proteinaceous substrate by reaction of an aziridine moiety and any nucleophilic functional group present on the proteinaceous substrate, such as, for example, carboxylic acid groups, amide groups, hydroxyl groups and sulfide groups or degradation products thereof.

In various preferred embodiments of the present invention, methods according to the invention can further include applying a topcoat composition to the primed substrate. As used herein, a "topcoat composition" includes, but is not limited to, decorative and protective coatings, additional adhesives and prosthetic materials, as well as multilayer applications such as a colorcoat and a final clearcoat. Decorative and protective coatings suitable for use in accordance with various embodiments of the present invention can be water-based or lacquer-based polishes. Preferred decorative and protective coatings for use in accordance with various embodiments of the present invention are water-based. Preferably, a topcoat composition is applied to the primed substrate shortly after, and even more preferably, immediately after removal of the solvent from the solution of a polyfunctional aziridine component in the solvent. Unreacted aziridine functionalities on the primed substrate can then react with carboxyl groups or other nucleophilic groups in the topcoat composition providing improved adhesion between the proteinaceous substrate and the topcoat composition.

The invention will now be described in further detail with reference to the following non-limiting examples.

EXAMPLES

Improvement of Adhesive Strength Testing

Comparison 1: Evaluation of Inventive Primer & Water-Based Nail Polish versus Current Market Leader Nitrocellulose Lacquer Based Nail Polish System.

Sixteen female subjects meeting the inclusion and exclusion criteria set forth below took part in the comparative evaluation. The inclusion criteria were: (i) between the ages of 18 and 65 years, inclusive; (ii) must have regularly used nail enamel at least once per week; (iii) must have had a relatively uniform nail length, which extended to or exceeded the fingertip; (iv) healthy nails; (v) completion of a medical history form and the understanding and signing of an Informed Consent Form; (vi) considered dependable and had the intelligence to follow directions; and (vii) must avoid gardening during the evaluation study. The exclusion criteria were: (i) no repaired nails; (ii) no recently removed tips or wraps; (iii) no onychophagy (nail biting), ridges and/or discoloration; (iv) no history of sensitivity to nail enamels or removers; (v) no occupational limitations, i.e., chemist, use of industrial cleaners; (vi) no evidence of excessive, non-reparable breakage; (vii) not in an occupation that pre-disposes nails to excessive breakage/exposure; and (viii) not pregnant or nursing.

The testing interval consisted of 8 days, with 4 evaluations. Subjects had their nails manicured and cleaned. All evidence of nail enamel was removed by a Licensed Cosmetologist. Subjects washed their hands with mild soap and water, thoroughly drying them prior to test material applications.

All test products were shaken just prior to use. Subjects were assigned numbers. Even numbered subjects had a nail coating system according to an inventive embodiment applied to the nails of their right hands and the comparative nail coating system applied to the nails of their left hands. Conversely, odd numbered subjects had the inventive embodiment applied to the nails of their left hands and the comparative nail coating system applied to the nails of their right hands.

The Inventive nail coating system used in this comparison was as follows: (i) inventive primer composition containing PZ-33 (a polyfunctional aziridine component, available from PolyAziridine, LLC, Medford, N.J.) in propylene glycol methyl ether, in an amount of 5% by weight of the solution, Lot 187601; (ii) Go Natural water-based polish color coat "I'm Looking Good", Lot 188304 (Go Natural available from Mad river Science, McKinleyville, Calif.); and (iii) Go Natural water-based topcoat, Lot 183805.

The Comparative nail coating system used was as follows: (i) OPI's "Chip Skip" primer, Lot NT100; (ii) OPI's "Natural Nail Basecoat", Lot NT T10; (III) OPI's Colorcoat "I'm Not Really A Waitress", Lot NT H08; (iv) OPI's "Top Coat", Lot NT T30. (OPI Product, Inc, North Hollywood, Calif.).

A very thin coat of the inventive primer or OPI primer and base coat was applied to all nails (according to the subject numbering described above), allowing it to dry for approximately 30 seconds or the time it took to apply to all the fingernails. One thin coat of applicable colorcoat was applied. A second thin coat of applicable colorcoat was applied and allowed to dry to the touch for 30 seconds. A generous coat of applicable topcoat was then applied and allowed to dry for 30 seconds. The fingernails were then blown dry for 60 seconds, with a blow dryer set on warm heat/low blower setting. Subjects remained at the facility for an additional 15 minutes to ensure adequate drying/curing.

Subjects were reminded not to use any nail products, base and/or top coats, including color touch-up. Subjects were instructed not to immerse their nails in hot/soapy water for at least 2 hours post application and to avoid activities that could damage their nails.

Evaluations were made for gloss on Days 0, 3, 5, and 7, and for chip and wear on Days 3, 5 and 7 by matching complimentary fingers on the left and right hands and scoring the individual fingers. The Licensed Cosmetologist conducted the evaluations.

The initial application of test materials revealed a perfect gloss evaluation. Seven days post-application, the inventive nail coating system significantly outperformed the comparative nail coating system, exhibiting less diminished gloss, less chipping and less diminished wear. As shown by this comparison, embodiments of the present invention can provide water-based, non-toxic nail coatings that perform as well as the market-leading nitrocellulose lacquer nail coating systems currently available to the consumer.

Comparison 2: Evaluation of Inventive Primer & Water-Based Nail Polish Versus Water-Based Nail Polish without Inventive Primer.

An evaluation using a laboratory test protocol similar to that described in Comparison 1, comparing water-based Go Natural nail polishes having the inventive primer solution used in Comparison 1 applied to the nail substrate before application, and the same water-based Go Natural nail polishes without the use of the inventive primer solution, was carried out over five (5) days on five (5) volunteer human subjects' fingernails for each polish tested. The overall average comparative results show that the use of the inventive primer solution markedly improves the adhesion performance of the Go Natural nail polish by an average of greater than 15%.

Comparison 3: Evaluation of Inventive Primer & Nitrocellulose Lacquer Based Nail Polish Versus Nitrocellulose Lacquer Based Nail Polish without Inventive Primer.

An evaluation using a laboratory test protocol similar to that described in Comparison 2, comparing acrylic lacquer based nail polishes having the inventive primer solution used in Comparison 1 applied to the nail substrate before application, and the same acrylic lacquer based nail polishes without the use of the inventive primer solution, was carried out over five (5) days on five (5) volunteer human subjects' fingernails for each polish tested. The overall average comparative results show that the use of the inventive primer solution markedly improves the adhesion performance of the nitrocellulose lacquer-based nail polish by an average of greater than 15%.

As shown in the comparisons set forth above, the present invention provides improved adhesion of various topcoat compositions to proteinaceous substrates versus direct application of the topcoat compositions to the substrate. Additionally as can also be seen from Comparison 1, the present invention can provide improved performance compared to an existing market-leading system consisting of a conventional base coat, color coat, and topcoat marketed by OPI.

In Vitro Toxicity Testing:

Solutions of a polyfunctional aziridine component in a suitable non-reactive solvent were evaluated for skin irritancy potential utilizing the MatTek Corporation (Ashland, Mass.) EpiDerm in vitro toxicity testing system.

MatTek's EpiDerm Skin Model consists of normal, human-derived epidermal keratinocytes (NHEK) which have been cultured to form a multilayered, highly differentiated model of the human epidermis. Keratinocytes are cultured on specially prepared, permeable cell culture inserts. This system closely parallels human skin. EpiDerm consists of highly organized basal, spinous, granular and cornified layers analogous to those found in vivo. Epiderm cultured keratinocytes are mitotically and metabolically active. EpiDerm, when used with the recommended cell metabolism assay as carried out in these Examples, can quickly provide toxicological profiles. The procedure utilizes a water-soluble, yellow, tetrazolium salt (MTT {3-4, 5-dimethylthiazol-2-yl]-2,5-diphenyl-tetrazolium bromide}), which is reduced by succinate dehydrogenase in the mitochondria of viable cells to a purple, insoluble formazan derivative. Substances which damage this mitochondrial enzyme inhibit the reduction of the tetrazolium salt. The amount of MTT reduced by a culture is therefore proportional to the number of viable cells.

An inventive test solution was prepared by dissolving a pentaerythritol tris(3-aziridinopropionate) composition (PZ-33™ polyfunctional aziridine, obtained from PolyAziridine LLC, Medford, N.J.) in propylene glycol n-butyl ether in an amount of 5% by weight, based on the solution.

After the appropriate tissue preparation according to the MatTek EpiDerm model, for each dosage of the inventive solution, one-hundred microliters of the solution were deposited on a piece of filter paper. After drying, a circular portion of the exposed filter paper, the diameter of the MatTek Millicell, was cut out and added to the Millicells containing the EpiDerm samples so that the inventive solution filter paper surface contacted the tissue. Each dosage was then moistened with one-hundred microliters of distilled water to ensure interaction between the solution-treated filter paper and the tissue. The six (6) well plates containing the dosed EpiDerm samples were then incubated at 37° C., five (5)% carbon dioxide and ≥90% humidity. After the appropriate exposure periods, each insert was individually removed from its plate and rinsed with phosphate buffered saline (PBS) to remove any residual material. Each was then rinsed a second time. Excess liquid was shaken off and each EpiDerm sample was placed into 300 microliters of MTT solution. The EpiDerm samples were then returned to the incubator. After the three (3) hour MTT exposure, each insert was removed and gently rinsed with PBS to remove any residual MTT solution. Excess PBS was shaken from each of the inserts, which were then blotted on the bottom using paper towels. The inserts were then each placed into one (1) well of a 24 well extraction plate. Each insert was then immersed in two (2) milliliters of extraction solution overnight. After the exposure, the liquid within each insert was decanted back into the well from which it was taken. The remaining extractant solution was then agitated and a 200 microliter aliquot of each extract was removed for evaluation. A Dynatech MR 4000 Automatic Microplate Reader was used to determine the absorbance of each extract at 570 nm. With the absorbance of the negative control defined as 100%, the percent absorbencies of the test article were determined. The percentages listed below directly correlate with the cell metabolism in the EpiDerm samples.

TABLE 2

MatTek EpiDerm Toxicity Results.

| Article (% & Exposure) | System | Percent Viability | Percent Inhibition |
|---|---|---|---|
| (100% - 1 hr.) | EpiDerm | 112 | −12 |
| (100% - 4.5 hr.) | EpiDerm | 76 | 24 |
| (100% - 20 hr.) | EpiDerm | 98 | 2 |

For the article, a semi-log scale was used to plot the percent viabilities, on the linear y axis, versus the dosing times, on the log x axis. By interpolation and where possible, the time at which the percent viability would be 50% (ET-50) was estimated.

The NB Code/Batch#: 187601; ID: 5% PZ 33 in PnB test article, at 100%*, elicited an ET-50 greater than 24 hours. According to MatTek Corporation, as a general guideline, the following groupings can be used in assigning expected in vivo irritancy responses based on the ET-50 results obtained using MatTek's EpiDerm:

TABLE 3

| ET-50 (hrs) | Expected In vivo Irritancy | Example |
|---|---|---|
| <0.5 | Severe, probably corrosive | Conc. Nitric Acid |
| 0.5-4 | Moderate | 1% Sodium Dodecyl Sulfate |
| 4-12 | Moderate to Mild | 1% Triton X-100 |
| 12-24 | Very Mild | Baby Shampoo |
| 24 | Non-irritating | 10% Tween 20 |

Under the conditions of this test, the NB Code/Batch#: 187601; ID: 5% PZ 33 in PnB test article, at 100%*, elicited an ET-50 greater than 24 hours and has an expected in vivo dermal irritancy potential in the non-irritating range.

Human Skin Testing/Insult Patch Testing:

The potential of a primer composition in an accordance with an embodiment of the present invention to induce primary or cumulative irritation and/or allergic contact sensitization of human skin was carried out according to the following procedure.

Participants:

Fifty-six (56) qualified subjects, male and female, ranging in age from 18 to 67 years, were selected for this evaluation. Fifty-four (54) subjects completed this study. The remaining subjects discontinued their participation for various reasons, none of which were related to the application of the Inventive primer composition.

Inclusion Criteria for the Study:

(i) Male and female subjects, age 16[a] and over; (ii) Absence of any visible skin disease which might be confused with a skin reaction from the test material; (iii) Prohibition of use of topical or systemic steroids and/or antihistamines for at least seven days prior to study initiation; (iv) Completion of a Medical History form and the understanding and signing of an Informed Consent form; and (v) Considered reliable and capable of following directions Exclusion Criteria for the Study:

(i) Ill health; (ii) Under a doctor's care or taking medication(s) which could influence the outcome of the study; (iii) Females who are pregnant or nursing; and (iv) A history of adverse reactions to cosmetics or other personal care products.

The Inventive primer composition evaluated in this study contained PZ-33 (a polyfunctional aziridine component, available from PolyAziridine, LLC, Medford, N.J.) in propylene glycol n-butyl ether, in an amount of 5% by weight of the solution.

Methodology:

The upper back between the scapulae served as the treatment area. Approximately 0.2 ml of the Inventive primer composition, or an amount sufficient to cover the contact surface, was applied to the 1"×1" absorbent pad portion of a clear adhesive dressing and allowed to volatilize for approximately 30 minutes. This was then applied to the appropriate treatment site to form a semi-occlusive patch.

Induction Phase:

Patches were applied three (3) times per week (e.g., Monday, Wednesday, and Friday) for a total of nine (9) applications. The site was marked to ensure the continuity of patch application. Following supervised removal and scoring of the first Induction patch, participants were instructed to remove all subsequent Induction patches at home, twenty-four hours after application. The evaluation of this site was made again just prior to re-application. If a participant was unable to report for an assigned test day, one (1) makeup day was permitted. This day was added to the Induction period.

With the exception of the first supervised Induction Patch reading, if any test site exhibited a moderate (2-level) reaction during the Induction Phase, application was moved to an adjacent area. Applications were discontinued for the remainder of this test phase, if a moderate (2-level) reaction was observed on this new test site. Applications would also be discontinued if marked (3-level) or severe (4-level) reactivity was noted.

Rest periods consisted of twenty-four hours following each Tuesday and Thursday removal, and forty-eight hours following each Saturday removal.

Challenge Phase:

Approximately two (2) weeks after the final Induction patch application. a Challenge patch (identical to Induction patch) was applied to a virgin test site adjacent to the original Induction patch site, following the same procedure described for Induction. The Induction phase assesses initial adverse reactions (contact dermatitis) to the test material. Since most allergic reactions are induced by allergens during some previous exposure or series of exposures, the Challenge phase is used to determine if the exposure during the induction phase did indeed create an allergic contact dermatitis. The Challenge patch was removed and the site scored at the clinic twenty-four and seventy two hours post-application.

Methodology (Continued): Evaluation Criteria (Erythema and Additional Dermal Sequelae):

| | |
|---|---|
| 0 = | No visible skin reaction |
| 0.5 = | Barely perceptible |
| 1 = | Mild |
| 2 = | Moderate |
| 3 = | Marked |
| 4 = | Severe |
| E = | Edema |
| D = | Dryness |
| S = | Staining |
| P = | Papules |
| V = | Vesicles |
| B = | Bullae |
| U = | Ulceration |
| Sp = | Spreading |

Erythema was scored numerically according to this key. If present, additional Dermal Sequelae were indicated by the appropriate letter code and a numerical value for severity.

The results of each participant are set forth below in the table. With one exception, observations remained within normal limits throughout the test interval. Subject #17 exhibited mild (1) erythema and edema seventy-two and ninety-six hours post challenge application. Unfortunately, this subject was unable to participate in a rechallenge patch test to better define the nature and reproducibility of this response.

The results of this Insult patch testing, as shown below in the table, indicate that the Inventive primer composition tested does not have a statistically significant potential for dermal irritation or allergic contact sensitization. Since no other dermal sequalae (spreading beyond the site, vesiculation) was observed, this response can be considered clinically insignificant.

Table of Insult Patch Test Results:

| Subject Number | 24*hr | \multicolumn{9}{c}{Induction Phase} | | | | | | | | | Virgin Challenge Site | |
|---|---|---|---|---|---|---|---|---|---|---|---|---|
| | | 1 | 2 | 3 | 4 | 5 | 6 | 7 | 8 | 9 | 24*hr | 72 hr |
| 1 | 0 | 0 | 0 | 0 | 0 | 0 | 0 | 0 | 0 | 0 | 0 | 0 |
| 2 | 0 | 0 | 0 | 0 | 0 | 0 | 0 | 0 | 0 | 0 | 0 | 0 |
| 3 | 0 | 0 | 0 | 0 | 0 | 0 | 0 | 0 | 0 | 0 | 0 | 0 |
| 4 | 0 | 0 | 0 | 0 | 0 | 0 | 0 | 0 | 0 | 0 | 0 | 0 |
| 5 | 0 | 0 | 0 | 0 | 0 | 0 | 0 | 0 | 0 | 0 | 0 | 0 |
| 6 | 0 | 0 | 0 | 0 | 0 | 0 | 0 | 0 | 0 | 0 | 0 | 0 |
| 7 | 0 | 0 | 0 | 0 | 0 | 0 | 0 | 0 | 0 | 0 | 0 | 0 |
| 8 | 0 | 0 | 0 | 0 | 0 | 0 | 0 | 0 | 0 | 0 | 0 | 0 |
| 9 | 0 | 0 | 0 | 0 | 0 | 0 | 0 | 0 | $2^{E2A}$ | 0 | 0 | 0 |
| 10 | 0 | 0 | 0 | 0 | 0 | 0 | 0 | 0 | 0 | 0 | 0 | 0 |
| 11 | 0 | 0 | 0 | 0 | 0 | 0 | 0 | 0 | 0 | 0 | 0 | 0 |
| 12 | 0 | 0 | 0 | 0 | 0 | 0 | 0 | 0 | 0 | 0 | 0 | 0 |
| 13 | 0 | 0 | 0 | 0 | 0 | 0 | 0 | 0 | 0 | 0 | 0 | 0 |
| 14 | 0 | 0 | 0 | 0 | 0 | 0 | 0 | 0 | 0 | 0 | 0 | 0 |
| 15 | 0 | 0 | 0 | 0 | 0 | 0 | 0 | 0 | 0 | 0 | 0 | 0 |
| 16 | 0 | 0 | 0 | 0 | 0 | 0 | 0 | 0 | 0 | 0 | 0 | 0 |
| 17 | 0 | 0 | 0 | 0 | 0 | 0 | 0 | 0 | 0 | 0 | $1^{E1}$ | $1^{E1*}$ |
| 18 | 0 | 0 | 0 | 0 | 0 | 0 | 0 | 0 | 0 | 0 | 0 | 0 |
| 19 | 0 | 0 | 0 | 0 | 0 | 0 | 0 | 0 | 0 | 0 | 0 | 0 |
| 20 | 0 | 0 | 0 | 0 | 0 | 0 | 0 | 0 | $2^{E2A}$ | $0.5^{D1}$ | 0 | 0 |
| 21 | 0 | 0 | 0 | 0 | 0 | 0 | 0 | 0 | 0 | 0 | 0 | 0 |
| 22 | 0 | 0 | 0 | | | | DID NOT COMPLETE | | | | | |
| 23 | 0 | 0 | 0 | 0 | 0 | 0 | 0 | 0 | 0 | 0 | 0 | 0 |

Table of Insult Patch Test Results:

| Subject Number | 24*hr | \multicolumn{9}{c}{Induction Phase} | \multicolumn{2}{c}{Virgin Challenge Site} |

| Subject Number | 24*hr | 1 | 2 | 3 | 4 | 5 | 6 | 7 | 8 | 9 | 24*hr | 72 hr |
|---|---|---|---|---|---|---|---|---|---|---|---|---|
| 24 | 0 | 0 | 0 | 0 | 0 | 0 | 0 | 0 | 0 | 0 | 0 | 0 |
| 25 | 0 | 0 | 0 | 0 | 0 | 0 | 0 | 0 | 0 | 0 | 0 | 0 |
| 26 | 0 | 0 | 0 | 0 | 0 | 0 | 0 | 0 | 0 | 0 | 0 | 0 |
| 27 | 0 | 0 | 0 | 0 | 0 | 0 | 0 | 0 | 0 | 0 | 0 | 0 |
| 28 | 0 | 0 | 0 | 0 | 0 | 0 | 0 | 0 | 0 | 0 | 0 | 0 |
| 29 | 0 | 0 | 0 | 0 | 0 | 0 | 0 | 0 | 0 | 0 | 0 | 0 |
| 30 | 0 | 0 | 0 | 0 | 0 | 0 | 0 | 0 | 0 | 0 | 0 | 0 |
| 31 | 0 | 0 | 0 | 0 | 0 | 0 | 0 | 0 | 0 | 0 | 0 | 0 |
| 32 | 0 | 0 | 0 | 0 | 0 | 0 | 0 | 0 | 0 | 0 | 0 | 0 |
| 33 | 0 | 0 | 0 | 0 | 0 | 0 | 0 | 0 | 0 | 0 | 0 | 0 |
| 34 | 0 | 0 | 0 | 0 | 0 | 0 | 0 | 0 | 0 | 0 | 0 | 0 |
| 35 | 0 | 0 | 0 | 0 | 0 | 0 | 0 | 0 | 0 | 0 | 0 | 0 |
| 36 | 0 | 0 | 0 | 0 | 0 | 0 | 0 | 0 | 0 | 0 | DNC | |
| 37 | 0 | 0 | 0 | 0 | 0 | 0 | 0 | 0 | 0 | 0 | 0 | 0 |
| 38 | 0 | 0 | 0 | 0 | 0 | 0 | 0 | 0 | 0 | 0 | 0 | 0 |
| 39 | 0 | 0 | 0 | 0 | 0 | 0 | 0 | 0 | 0 | 0 | 0 | 0 |
| 40 | 0 | 0 | 0 | 0 | 0 | 0 | 0 | $0^{D1}$ | 0 | 0 | 0 | 0 |
| 41 | 0 | 0 | 0 | 0 | 0 | 0 | 0 | 0 | 0 | 0 | 0 | 0 |
| 42 | 0 | 0 | 0 | 0 | 0 | 0 | 0 | 0 | 0 | 0 | 0 | 0 |
| 43 | 0 | 0 | 0 | 0 | 0 | 0 | 0 | 0 | 0 | 0 | 0 | 0 |
| 44 | 0 | 0 | 0 | 0 | 0 | 0 | 0 | 0 | 0 | 0 | 0 | 0 |
| 45 | 0 | 0 | 0 | 0 | 0 | 0 | 0 | 0 | 0 | 0 | 0 | 0 |
| 46 | 0 | 0 | 0 | 0 | 0 | 0 | 0 | 0 | 0 | 0 | 0 | 0 |
| 47 | 0 | 0 | 0 | 0 | 0 | 0 | 0 | 0 | 0 | 0 | 0 | 0 |
| 48 | 0 | 0 | 0 | 0 | 0 | 0 | 0 | 0 | 0 | 0 | 0 | 0 |
| 49 | 0 | 0 | 0 | 0 | 0 | 0 | 0 | 0 | 0 | 0 | 0 | 0 |
| 50 | 0 | 0 | 0 | 0 | 0 | 0 | 0 | 0 | 0 | 0 | 0 | 0 |
| 51 | 0 | 0 | 0 | 0 | 0 | 0 | 0 | 0 | 0 | 0 | 0 | 0 |
| 52 | 0 | 0 | 0 | 0 | 0 | 0 | 0 | 0 | 0 | 0 | 0 | 0 |
| 53 | 0 | 0 | 0 | 0 | 0 | 0 | 0 | 0 | 0 | 0 | 0 | 0 |
| 54 | 0 | 0 | 0 | 0 | 0 | 0 | 0 | 0 | 0 | 0 | 0 | 0 |
| 55 | 0 | 0 | 0 | 0 | 0 | 0 | 0 | 0 | 0 | 0 | 0 | 0 |
| 56 | 0 | 0 | 0 | 0 | 0 | 0 | 0 | 0 | 0 | 0 | 0 | 0 |

24* = Supervised removal of $1^{st}$ Induction and Challenge Patch
A = Changed to adjacent site
*= Observation conducted 96 hours post challenge application
E = Edema
D = Dryness
DNC = Did not complete study Both the MatTek EpiDerm model toxicity testing and the human skin insult patch testing carried out using an inventive example of a solution in accordance with an embodiment of the present invention, show that the solutions are non-toxic, non-irritant and safe. This is surprising and unexpected given the dangers associated with azacyclopropane and polyethylenimine.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A non-toxic, nail primer composition consisting essentially of a solution of a polyfunctional aziridine component in a non-reactive solvent, wherein the polyfunctional aziridine component comprises pentaerythritol tris(3-aziridinopropionate), wherein the non-reactive solvent comprises a glycol monoalkyl ether, and wherein the polyfunctional aziridine component is present in an amount of at least about 0.5% by weight, based on the solution.

2. The non-toxic, nail primer composition according to claim 1, wherein the polyfunctional aziridine component is present in an amount of 1 to 10% by weight, based on the solution.

3. The non-toxic, nail primer composition according to claim 1, wherein the polyfunctional aziridine component is present in an amount of 2.5 to 7.5% by weight, based on the solution.

4. The non-toxic, nail primer composition according to claim 1, wherein the polyfunctional aziridine component comprises a mixture of two or more compounds having two or more aziridine functionalities and the component has an average aziridine functionality of ≥3.0.

5. The non-toxic, nail primer composition according to claim 1, wherein the polyfunctional aziridine component further comprises a compound selected from the group consisting of trimethylolpropane tris(3-2-methylaziridino) propionate, trimethylolpropane tris(3-aziridinopropionate), and mixtures thereof.

6. The non-toxic, nail primer composition according to claim 5, wherein the polyfunctional aziridine component is present in an amount of 2.5 to 7.5% by weight, based on the solution.

7. The non-toxic, nail primer composition according to claim 1, wherein the non-reactive solvent comprise a propylene glycol monoalkyl ether.

8. The non-toxic, nail primer composition according to claim 1, wherein the non-reactive solvent comprises propylene glycol monomethyl ether.

9. A non-toxic, nail primer composition consisting essentially of a solution of a polyfunctional aziridine component in propylene glycol mono-methyl ether, wherein the polyfunctional aziridine component comprises pentaerythritol tris(3-aziridinopropionate), and wherein the polyfunctional aziridine component is present in an amount of 0.5 to 10% by weight, based on the solution.

10. A non-toxic, nail primer composition consisting essentially of a solution of a polyfunctional aziridine component in a non-reactive solvent, wherein the polyfunctional aziridine component is present in an amount of at least about 0.5% by weight, based on the solution.

* * * * *